United States Patent [19]

Demarne

[11] 3,933,853

[45] Jan. 20, 1976

[54] INDOLE DERIVATIVES

[75] Inventor: Henri Demarne, Montpellier, France

[73] Assignee: Clin Midy, France

[22] Filed: Feb. 16, 1973

[21] Appl. No.: 333,344

[30] Foreign Application Priority Data

Feb. 16, 1972 France.............................. 72.05197

[52] U.S. Cl...... 260/326.15; 260/296 R; 260/319.1; 260/326.13 R; 260/326.16; 424/274
[51] Int. Cl.²........................................ C07D 209/14
[58] Field of Search....... 260/326.16, 326.15, 296 R

[56] References Cited
UNITED STATES PATENTS 3,501,465   3/1970   Shen et al.................. 260/326.16 X

OTHER PUBLICATIONS

Julia et al., *Chemical Abstracts*, Vol. 66, 45920d (1967).
Julis et al. (II), *Bull Soc. Chim France*, 1966 No. 7, pp. 2291–2295 (1966).

*Primary Examiner*—Richard J. Gallagher
*Assistant Examiner*—Diana G. Rivers
*Attorney, Agent, or Firm*—Armstrong, Nikaido & Wegner

[57] ABSTRACT

Indoles of the formula

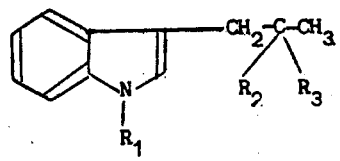

in which $R_1$ is phenyl, halophenyl, nitrophenyl, aminophenyl, lower alkoxyphenyl, pyridyl, benzyl, halobenzyl, lower alkoxybenzyl or a group of the formula —$C_nH_{2n}NR_4R_5$ in which $n$ is 2, 3 or 4 and each of $R_4$ and $R_5$ is hydrogen or alkyl, $R_2$ is hydrogen, $R_3$ is hydroxyl or $R_2$ and $R_3$ taken together are oxygen or $NOR_6$ in which $R_6$ is hydrogen, lower alkyl, lower acyl or a group of the formula —$C_mH_{2m}NR_7R_8$ in which $m$ is 2, 3 or 4 and each of $R_7$ and $R_8$ is lower alkyl, as well as the salts thereof with acids are of low toxicity and possess a pronounced analgesic effect and/or tranquillising effect and are of use in human and veterinary medicine.

4 Claims, No Drawings

INDOLE DERIVATIVES

This invention relates to derivatives of acetonyl indole, to their preparation and to their use in therapeutics.

According to the present invention there is provided a 1,3-disubstituted indole having the general formula

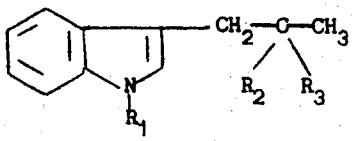

in which $R_1$ is a phenyl, halophenyl, nitrophenyl, aminophenyl or lower alkoxyphenyl group, a 2-, 3- or 4-pyridyl group, a benzyl, halobenzyl or lower alkoxybenzyl group or a group of the general formula $-C_nH_{2n}NR_4R_5$ in which $n$ is 2, 3 or 4 and each of $R_4$ and $R_5$ is a hydrogen atom or an alkyl group, $R_2$ is a hydrogen atom and $R_3$ is an hydroxyl group or $R_2$ and $R_3$ taken together represent an oxygen atom or a group of the formula $=NOR_6$ in which $R_6$ is a hydrogen atom, a lower alkyl group, a lower acyl group or a group of the formula $-C_mH_{2m}NR_7R_8$ in which $m$ is 2, 3 or 4 and each of $R_7$ and $R_8$ is a lower alkyl group, and salts thereof with pharmacologically acceptable mineral and organic acids.

Of especial interest are those compounds in which $R_1$ is a dimethylaminoethyl, dimethylaminopropyl, diethylaminoethyl or diethylaminopropyl group, when $R_2$ is a hydrogen atom and $R_3$ a hydroxyl group or when $R_2$ and $R_3$ taken together represent an oxygen atom or when $R_6$ is a hydrogen atom, a dimethylaminoethyl, a diethylaminoethyl, an acetyl or a propionyl group, and salts thereof with pharmacologically acceptable mineral and organic acids.

As examples of pharmacologically acceptable acids there may be mentioned hydrochloric acid, maleic acid, fumaric acid and citric acid.

The compounds of the present invention are ketones, the corresponding secondary alcohols and the corresponding ketoximes in which the hydroxyl group may have been etherified or esterified. According to a feature of the invention the ketones, i.e. those compounds in which $R_2$ and $R_3$ together represent an oxygen atom are prepared by treating a cyclic acetal having the general formula in which $R_1$ is as defined above with a mineral acid.

The corresponding alcohols, i.e. those compounds in which $R_2$ is a hydrogen atom and $R_3$ an hydroxyl group, may be obtained by the action of a metal hydride such as an alkali metal borohydride or lithium aluminium boride or by the action of hydrogen in the presence of a hydrogenation catalyst, such as Raney nickel.

The ketones may be converted into the corresponding oximes by the conventional methods e.g. using a hydroxylamine salt such as the hydrochloride or acetate in the presence of an aqueous solution of an alkali metal acetate, such as sodium acetate. The oximes may then be converted into those derivatives which are obtainable by esterification or etherification of the hydroxyl group attached to the oxime nitrogen atom making use of the known methods of etherification and esterification. Thus for esterification of the oxime there may be used a lower acid halide, such as the acid chloride e.g. acetyl chloride or propionyl chloride or an acid anhydride of a lower organic carboxylic acid such as acetic anhydride, propionyl anhydride and butyryl anhydride. For the etherification of the oxime there is ued a lower alkyl halide or a diaminoalkyl halide having the general formula $XC_mH_{2m}NR_7R_8$ in which X is a halogen atom, $m$ is 2, 3 or 4 and $R_7$ and $R_8$ are lower alkyl groups. The etherification reaction may be carried out in the presence of sodium hydride in a dipolar aprotic solvent such as dimethyl formamide. Examples of suitable lower alkyl halides are ethyl bromide and iodide, n-butyl bromide and iodide and isobutyl bromide and iodide. Examples of suitable dialkylaminoalkyl halides are dimethylaminoethyl chloride and bromide, diethylaminoethyl iodide, dibutylaminopropyl iodide and diethylaminobutyl bromide. In addition to sodium hydride other alkali metal hydrides such as potassium or lithium hydride may be used and other dipolar aprotic solvents. The reaction mixture should be rendered alkaline with sodium or potassium hydroxide or carbonate, or equivalent base, before the compound is isolated.

The reactions which take place are shown upon the appended flowsheet:

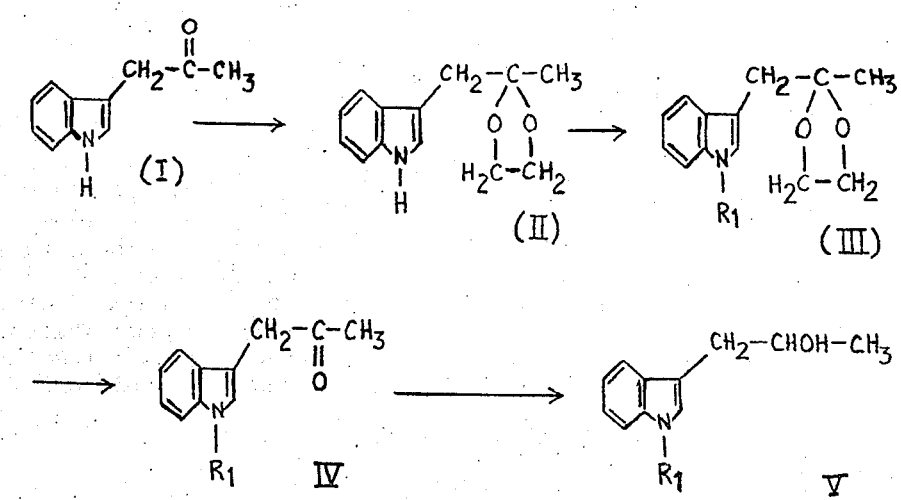

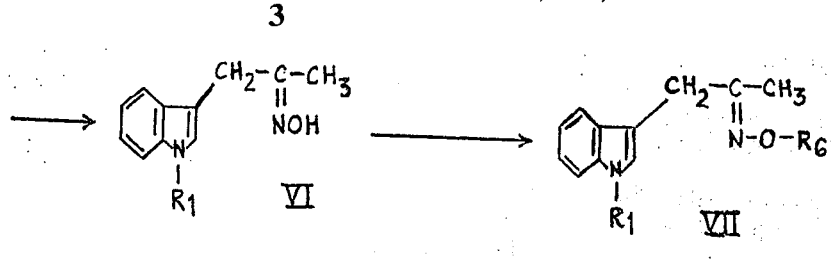

The ketone compound I may be obtained from the corresponding indole by a conventional synthesis (see *Journal of the Chemical Society*, 1965, page 4859).

The cyclic acetal II may be prepared by the action of ethylene glycol upon the ketone I in the presence of a dehydrating agent.

The acetals III carrying a substituent in the 1-position may be obtained by the action upon the acetal II either of an appropriately substituted iodobenzene in the presence of copper powder and sodium carbonate or potassium carbonate in a solvent having a high boiling point such as anisole, or by the action of an alkyl or dialkylaminoalkyl halide in the presence of sodium hydride in the presence of a dipolar aprotic solvent such as dimethylformamide.

The following examples illustrate the invention. All temperatures are in degrees centigrade. The melting points are marked (k) when they are determined using a Kofler block and (c) when they are determined using a capillary tube. The boiling points are those of the heating baths employed.

EXAMPLE I a. 3-[2-(1,3-dioxolanyl)propyl]indole.

86.5 g (0.5 mole) of 3-(2-oxopropyl)indole are dissolved in 1 liter of dry benzene in a flask equipped with a water separator. 43.4 g of ethylene glycol and 2 g of paratoluene sulphonic acid are added. The reaction mixture is held under reflux for 4 hours and then after slightly cooling poured into 1200 ml of a 12% aqueous solution of sodium carbonate. This is stirred, filtered and the residue washed with hot benzene. The organic phase is washed in water, dried, and the solvent removed under reduced pressure. The residue is then distilled at low pressure. Boiling point = 175°–180°/0.1 mm Melting point (k) (isopropylether) = 105°. Product = 87.3 g. Yield = 80%.

b. 3-[2-(1,3-dioxolanyl)propyl]-1-phenylindole 40.8 g (0.2 mole) of freshly distilled iodobenzene are added to 21.7 g (0.1 mole) of 3-[2-(1,3-dioxolanyl)propyl]indole in 400 ml of bromobenzene. After solution has taken place 100 g of potassium carbonate and 55 g of copper powder are added. The reaction mixture is held at reflux for 36 hours, the product filtered and distilled, after removing the solvent and the excess of iodobenzene under reduced pressure. A yellow oil is collected. Boiling point = 210°–215°/0.1 mm. Product = 27.9 g: Yield = 95%.

c. 3-(2-oxopropyl)-1-phenylindole (code number 5944) 16.7 g (0.057 mole) of the cyclic acetal obtained as described above are dissolved in 150 ml of 96% ethyl alcohol. 10 ml of hydrochloric acid (5N) are added and the reaction mixture held at boiling point for 30 minutes. The whole of the alcohol is removed and the residue obtained is distilled. Boiling point = 195°–205°/0.1 mm.

The oil obtained is recrystallised from di-isopropyl ether. Product = 12 g. Melting point (k) = 72°: Yield = 86%.

EXAMPLE 2

1-(4-methoxyphenyl)-3-(2-hydroxypropyl)indole (code number 5992).

5.6 G (0.02 mole) of 1-(4-methoxyphenyl)-3-(2-oxopropyl)indole, prepared as described in example 1 but using 4-methoxyiodobenzene instead of iodobenzene are dissolved in 50 ml of anhydrous ethanol in a 200 ml autoclave. 2 g of Raney nickel are added. The autoclave is brought to a pressure of 50 kg of hydrogen and heat is applied at 100° for 8 hours at this pressure. The reaction medium is taken to dryness and the residue dissolved in normal acetic acid in the presence of diethyl ether. The organic phase is dried and the solvents are removed. The residue is then distilled.

Boiling point = 210° to 220°/0.1mm. Recrystallisation is carried out from di-isopropyl ether. Product = 3.1 g: Melting point (k) = 160° Yield = 55 %.

EXAMPLE 3

1-(2-chlorophenyl)-3-(2-hydroxyiminopropyl)indole (code number 5989).

2.1 G (0.03 mole) of hydroxylamine hydrochloride and 2.1 g of sodium acetate are added, all at once, to 5.8 g (0.02 mole) of 1-(2-chlorophenyl)-3-(2-oxopropyl)indole prepared as described in example 1 but using 2-chloroiodobenzene instead of iodobenzene are dissolved in 50 ml of ethanol. The mixture is stirred overnight. The oxime formed is then filtered, washed in water and recrystallised, after drying, from 30 ml of di-isopropyl ether. Product = 4.3 g: Melting point (k) = 127°. Yield = 71%.

EXAMPLE 4 a. 1-(2-dimethylaminoethyl)-3-[2-(1,3-dioxolanyl)propyl]-indole and its maleate.

3 G of sodium hydride in 50% suspension in oil are added to a solution of 11 g (0.05 mole) of 3-[2-(1,3-dioxolanyl)propyl]-indole in 110 ml of dry dimethylformamide. After 10 minutes stirring, 6 g of 1-chloro-2-dimethylaminoethane are added and stirring carried out for 4 hours at 20°. The resulting product is poured into water, extracted with diethyl ether and the ethereal phase is then extracted with dilute acetic acid. The aqueous phase is made alkaline with dilute soda, the base is extracted with diethyl ether, the ethereal solution is dried and the ether is removed. The residual oil obtained is distilled: Boiling point = 185°–190°/0.1 mm, product = 8.6 g. The oil obtained is treated in solution in acetone with 4.1 g of maleic acid and the salt obtained is recrystallised from ethyl acetate. Weight of salt = 8.1 g. Melting point (k) = 123°.

b. 1-(2-dimethylaminoethyl)-3-(2-oxopropyl)indole (code number 5353) and its maleate.

19.6 G of 1-(2-dimethylaminoethyl)-3-[2(1,3-dioxolanyl)-propyl]indole are treated with 5N hydrochloric acid on a water bath for half an hour. the reaction mixture is rendered alkaline with soda, extracted with diethyl ether, dried and the ether removed. The oil obtained is distilled. Boiling point = 160°–170°/0.1 mm. Weight of product = 15.8 g.

The base obtained is treated with 7.5 g of maleic acid dissolved in 30 ml of ethyl acetate. The maleate crystallises upon cooling. Melting point (k) = 107-109°

EXAMPLE 5

1-(2-dimethylaminoethyl)-3-[2-(2-dimethylaminoethyl oxyimino)propyl]indole (code number 5444) and its acid dimaleate.

17 G (0.065 mole) of 1-(2-dimethylaminoethyl)-3-(2-hydroxyiminopropyl)indole are treated in 90 ml of anhydrous dimethylformamide with 3.7 g of sodium hydride in 50% suspension in an oil extracted from petroleum. After 10 minutes stirring, 7.7 g of 1-chloro-2-dimethylaminoethane are added, all at once. The reaction mixture is maintained at 65° for 4 hours, then cooled and poured into water. Extraction is affected with diethyl ether and the organic phase thus obtained is extracted with dilute acetic acid. The aqueous phase is made alkaline with a dilute solution of caustic potash and is extracted with diethyl ether. The organic phase thus extracted is dried and distilled to dryness. The residual oil is distilled at low pressure. Boiling point = 195°–210°/0.1 mm. Weight of product = 15 g.

14.3 of this oil are treated with 10 g of maleic acid dissolved in acetone. The salt obtained is filtered and recrystallised from a mixture of acetone and ethyl acetate. Melting point (k) = 112°. Weight of product = 16 g.

EXAMPLE 6

1-(2-dimethylaminoethyl)-3-(2-hydroxypropyl)indole (code number 5607) and its hydrochloride.

During the course of 30 minutes, 1.8 g of sodium hydroboride are added to 8.5 g of 1-(2-dimethylaminoethyl)-3-(2-oxopropyl)indole dissolved in 40 ml of methanol and the whole allowed to stand for 1 hour. The solvent is removed, the residue dissolved in water, and extracted with diethyl ether. The ethereal phase is washed and dried, the solvent evaporated, and the residue distilled at low pressure. Boiling point = 170°–180°/0.1 mm. Weight of product = 6 g: Yield = 72%.

When dissolved in dry diethyl ether and treated with hydrochloric acid gas the compound is converted into the hydrochloride which precipitates. After recrystallisation from isopropanol, the hydrochloride (4.5 g) melts at 150°(k).

EXAMPLE 7

1-(2-dimethylaminoethyl)-3-(2-hydroxyiminopropyl)-indole (code number 5354) and its acid maleate.

A solution of 2.85 g of hydroxylamine hydrochloride in 20 ml of water, and then 2.8 g of sodium acetate, are added to 6.6 g (0.025 mole) of 1-(2-dimethylaminoethyl)-3-(2-oxopropyl)-indole dissolved in 75 ml of 96% ethyl alcohol. The mixture is refluxed for two and a half hours, the alcohol evaporated and the residue dissolved in water. The solution is rendered alkaline with an aqueous solution of sodium carbonate, extracted with diethyl ether and the ethereal extract washed with water. The ethereal extract is dried and the ether evaporated. The crude oxime thus obtained is dissolved in 25 ml of ethyl acetate. A hot solution of 2.5 g of maleic acid in ethyl acetate and 5 ml of acetone is added whilst gently heating. The salt formed crystallises on cooling. The salt is filtered and recrystalled from acetone. Weight of product = 4.3 g: Yield = 48%. Melting point (k) = 142°.

EXAMPLE 8

1-(2-dimethylaminoethyl)-3-(2-acetoxyiminopropyl)-indole (code number 5472) and its acid maleate.

6.2 G (0.024 mole) of 1-(2-dimethylaminoethyl)-3-(2-hydroxyiminopropyl)indole are dissolved in 20 ml of acetic anhydride and are kept at 60° for 20 minutes. The excess of acetic anhydride is then removed under reduced pressure, the residue dissolved in a dilute aqueous solution of sodium carbonate, extracted with diethyl ether, the ether extract dried and the ether removed. The residue obtained is dissolved in ethyl acetate and treated whilst hot with 1.9 g of maleic acid. The salt formed is filtered. 2.9 g of product are collected having the appearance of a gum; the melting point is indeterminate.

EXAMPLE 9

1-(2-chlorobenzyl)-3-(2-hydroxyiminopropyl)indole (code number 5930).

2.5 G of hydroxylamine hydrochloride and 2.5 g of sodium acetate dissolved in 10 ml of water are added to 2 g (0.023 mole) of 1-(2-chlorobenzyl)-3-(2-oxopropyl)indole dissolved in 100 ml of 96% ethyl alcohol. Stirring takes place for 12 hours at 20° and the oxime formed is filtered. The product is recrystallised from di-isopropyl ether.

Melting point (k) = 100°. Yield = 79%.

EXAMPLE 10 a. 1-(4-aminophenyl)-3-[2-(1,3-dioxolan-2-yl)propyl]-indole.

3.4 G of 1-(4-nitrophenyl)-3-[2-(1,3-dioxolan-2-yl)propyl]-indole are dissolved in 80 ml of ethyl acetate and are reduced with hydrogen in the presence of 300 mg of 5% palladium on a carbon substrate. The reaction is exothermic. After the required volume of hydrogen has been absorbed, the reaction medium is filtered and the solvents removed. The residual amine is distilled. Boiling point = 260°–270°/0.1 mm. Weight of product = 2.8 g: Yield = 93%. Recrystallisation is from di-isopropyl ether. Melting point (k) = 123°.

b. 1-(4-aminophenyl)-3-(2-oxopropyl)indole (code number 5853).

Preceding as described in Example 1c, the cyclic acetal prepared as described above is converted into the indolyl acetone referred to above. After recrystallisation from ethyl acetate, it melts at 135° (k).

EXAMPLES 11 to 38

Proceeding as described in the foregoing examples, the compounds which are identified in tables 1a and 1b below by their code number, and by the meanings of the symbols used in general formula 1 and by the melting point of the base, or of one of its salts, are obtained. The compounds described in Examples 1 to 10 are also included in tables 1a and 1b.

TABLE 1a

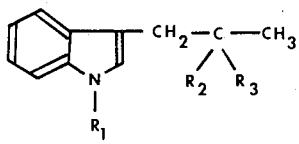

| Example No. | Code No. | $R_1$ | $R_2$ or $R_3$ / $R_2$ and $R_3$ together | | Salt, base or other derivatives | Mpt. Kofler = k Capillary = c | Recrystallising solvent |
|---|---|---|---|---|---|---|---|
| 1 | 5944 | —C₆H₅ | =O | | | 73° (k) | isopropyl ether |
| 11 | 5943 | do. | H | OH | | 69° (k) | butyl ether |
| 2 | 5992 | —C₆H₄—OCH₃ | H | OH | | 106° (k) | di-isopropyl ether |
| 12 | 5770 | do. | =NOH | | | 120° (k) | di-isopropyl ether |
| 13 | 5953 | —C₆H₄—Cl | =O | | semicarbazone | 204° (k) | ethanol + ethyl acetate |
| 14 | 5858 | —C₆H₄—Cl | H | OH | | 106° (k) | di-isopropyl ether |
| 15 | 5939 | —C₆H₄—F | =O | | | 55–58° (k) | di-isopropyl ether |
| 16 | 5940 | —C₆H₄—NO₂ | =O | | | 77° (k) | di-isopropyl ether |
| 17 | 5941 | do. | H | OH | | 112° (k) | di-isopropyl ether + butylether |
| 18 | 5934 | —C₆H₄—NH₂ | =N—OH | | base | 152° (k) | di-isopropyl ether |
| 19 | 5440 | —CH₂—C₆H₅ | =NOH | | | 136° (k) | ethyl acetate |
| 20 | 5928 | do. | H | OH | acid phthalate | 153° (k) | di-isopropyl ether |
| 21 | 5766 | —CH₂—C₆H₄—Cl | =O | | semicarbazone | 124° (k) | ethanol |
| 22 | 5963 | —CH₂—C₆H₄—F | =NOH | | | 127° (k) | di-isopropyl ether |
| 9 | 5930 | —CH₂—C₆H₄—Cl | =NOH | | | 100° (k) | di-isopropyl ether |
| 23 | 5857 | —C₆H₄—F | =NOH | | | 130° (k) | di-isopropyl ether |

TABLE 1a-continued

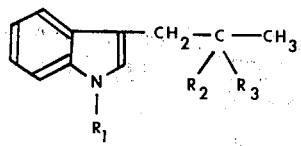

| Example No. | Code No. | $R_1$ | $R_2$ or $R_2$ and $R_3$ together | $R_3$ | Salt, base or other derivatives | Mpt. Kofler = k Capillary = c | Recrystallising solvent |
|---|---|---|---|---|---|---|---|
| 24 | 5936 | do. | H | OH | | 93° (k) | di-isopropyl ether |
| 25 | 5850 | –⟨⟩–NO₂ | =O | | | 90°–92° (k) | ethanol |
| 26 | 5852 | do. | H | OH | | 120° (k) | ethyl acetate |
| 10 | 5853 | –⟨⟩–NH₂ | =O | | base | 135° (k) | ethyl acetate |
| 27 | 5854 | –⟨⟩–NH₂ | H | OH | base | 106–108° (k) | di-isopropyl ether |
| 28 | 5985 | –⟨⟩–Cl | H | OH | | 114° (k) | di-isopropyl ether |
| 3 | 5989 | do. | =N—OH | | | 127° (k) | di-isopropyl ether |
| 29 | 6052 | –⟨⟩–F | =N—OH | | | 112° (k) | di-butyl ether |
| 30 | 5931 | –CH₂–⟨⟩–Cl | H | OH | acid phthalate | 155° (k) | diethyl ether di-isopropyl ether |

TABLE 1b

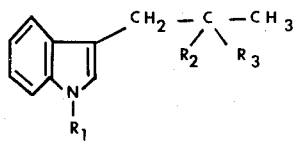

| Example No. | Code No. | $R_1$ | $R_2$ or $R_2$ and $R_3$ together | $R_3$ | Salt or base | M.pt Kofler = k capillary = c | Recrystallising solvent |
|---|---|---|---|---|---|---|---|
| 4 | 5353 | –(CH₂)₂–N(CH₃)(CH₃) | =O | | acid maleate | 107–109° (k) | ethyl acetate |
| 7 | 5354 | do. | =NOH | | acid maleate | 142° (k) | acetone |
| 8 | 5472 | do. | =NOCOCH₃ | | acid maleate | indeterminate | indeterminate |
| 31 | 5473 | do. | =NOCOCH₂CH₃ | | acid maleate | indeterminate | |
| 5 | 5444 | do. | =NOCH₂CH₂N(CH₃)(CH₃) | | acid dimaleate | 112° (k) | acetone + ethyl acetate |
| 6 | 5607 | do. | H | OH | hydrochloride | 150° (k) | isopropanol |
| 32 | 5477 | –(CH₂)₂N(CH₂CH₃)(CH₂CH₃) | =O | | citrate | 106° (k) | ethanol + ethyl acetate |
| 33 | 5938 | do. | H | OH | citrate | 106° (k) | ethanol + ethyl acetate |
| 34 | 5680 | do. | =NOCH₂CH₂N(C₂H₅)(C₂H₅) | | dicitrate | 131–133° (k) | ethanol |

TABLE Ib-continued

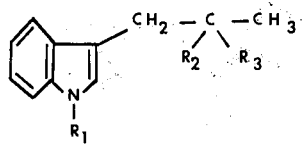

| Example No. | Code No. | $R_1$ | $R_2$ or $R_2$ and $R_3$ together | $R_3$ | Salt or base | M.pt Kofler = k capillary = c | Recrystallising solvent |
|---|---|---|---|---|---|---|---|
| 35 | 5370 | $-(CH_2)_3N\begin{smallmatrix}CH_3\\CH_3\end{smallmatrix}$ | =O | | acid maleate | 78° (c) | ethyl acetate |
| 36 | 5371 | do. | =NOH | | base | 103° (k) | di-isopropyl ether |
| 37 | 5771 | $-(CH_2)_3NHCH_3$ | =O | | citrate | 96–98° (k) | ethanol + ethyl acetate |

The properties of certain of the cyclic acetals used as intermediates in the preparation of the compounds described in the foregoing examples appear in table II below. These cyclic acetals are new and form a part of the present invention.

TABLE II

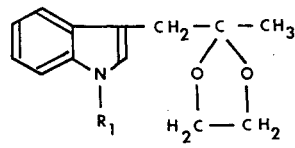

| Code No. | $R_1$ | Melting point | Recrystallising solvent (salt) |
|---|---|---|---|
| 5856 | —⟨C₆H₄⟩—Cl | 105° (k) | di-isopropyl ether |
| 5851 | —⟨C₆H₄⟩—F | 77° (k) | di-isopropyl ether |
| 5769 | —⟨C₆H₄⟩—OCH₃ | 77° (k) | ethanol + di-isopropyl ether |
| 5778 | —⟨C₆H₄⟩—NO₂ | 142° (k) | ethanol |
| 5779 | —⟨C₆H₄⟩—NH₂ | 123° (k) | di-isopropyl ether |
| 5990 | —⟨C₆H₄⟩ (Cl ortho) | 122° (k) | di-isopropyl ether |
| 5986 | —⟨C₆H₄⟩ (F ortho) | 95° (k) | ethanol + di-isopropyl ether |
| 5372 | —CH₂—⟨C₆H₅⟩ | 52° (c) | di-isopropyl ether |

TABLE II-continued

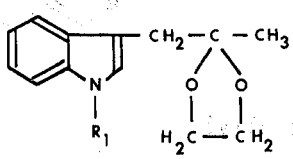

| Code No. | R₁ | Melting point | Recrystallising solvent (salt) |
|---|---|---|---|
| 5673 | $-CH_2-\langle\text{C}_6H_4\rangle-Cl$ (para) | 82° (k) | isopropyl alcohol |
| 5955 | $-CH_2-\langle\text{C}_6H_4\rangle$-Cl (ortho) | 112° (k) | di-isopropyl ether |
| 5352 | $-CH_2CH_2N(CH_3)_2$ | 123° (k) | ethyl acetate (acid maleate) |
| 5431 | $-CH_2CH_2N(C_2H_5)_2$ | 105° (k) | ethyl acetate (acid maleate) |
| 5355 | $-(CH_2)_3N(CH_3)_2$ | 104° (k) | ethyl acetate (acid maleate) |
| 5765 | $-(CH_2)_3NHCH_3$ | 132° (k) | ethyl acetate (acid maleate) |

The products of the present invention have been subjected to various pharmocodynamic tests particularly in respect of their analgesic effect and their tranquillising effect.

ANALGESIC EFFECT

A visceral pain is induced in the mouse by intraperitonal injection of a dilute solution of acetic acid (Koster and Anderson test).

The animals, which are starved on the day before the experiment, and separated into random batches of five, are treated with the products under test 30 minutes before injection of the irritant. Treatment was always performed orally.

After the acetic solution is injected the animals show symptoms of pain (stretching of the abdomen with extension of the back feet) which are counted during two spells of five minutes for each lot: from the fifth to the tenth minute and from the fifteen to the twentieth minute respectively after the acid is injected.

The products are tested using increasing doses and the 50% effective dose ($ED_{50}$ which reduces by one half the number of symptoms of pain exhibited is determined for a control batch of mice for each substance under test.

The $ED_{50}$ value is expressed in mg per kg bodyweight.

EFFECT ON THE CENTRAL NERVOUS SYSTEM

Exploration test (perforated board): the number of holes explored by an animal (mouse) which has unrestricted movement and is placed on the board for the first time, are recorded. This test demonstrates the curiosity or, more probably, a certain state of anxiety, in an animal which is placed in an environment with which it was previously unfamiliar.

As regards the analgesic effect, the values obtained with the following compounds may be especially noted

| Code | $ED_{50}$ (mg/kg) |
|---|---|
| 5607 | 0.75 |
| 5472 | between 0.75 and 1.5 |
| 5473 | do. |
| 5353 | 1.5 |
| 5354 | 3 |
| 5938 | 1.5 |
| 5444 | between 6.25 and 12.5 |

These doses were obtained by oral administration of the products of the invention.

As regards tranquillising effect, No. 5992, the $ED_{50}$ of which is 1 mg/kg bodyweight, and Nos. 5353 and 5472, for which the $ED_{50}$ values are 5 mg per kg bodyweight when administered by the oral route, may be particularly noted.

Moreover, the compounds of the present invention are not, in general, very toxic. By way of example, with the mouse, the dose which caused the death of 50% of the animals (or $LD_{50}$) is 800 mg/kg body weight when administered by the sub-cutaneous route and is greater than 800 mg/kg body weight when administered orally in the case of No. 5607.

Toxicity, expressed in mg/kg bodyweight, is given below for certain other compounds when administered by the sub-cutaneous route and by the oral route.

| Code | Route | |
|---|---|---|
| No. | sub-cutaneous | oral |
| 5477 | 200 | 400 |
| 5992 | >400 | >400 |
| 5472 | 400 | 200 |
| 5473 | 200-400 | >400 |

The substances may be used in human medicine for treating painful conditions which are either spontaneously generated or of surgical origin, and also psychoneurolgical afflictions such as anxiety.

The active ingredients will preferably be present in forms suitable for oral, parenteral, local or endorectal administration, such, for example, as tablets, drops, syrups, powders, suppositories or injectable liquids.

It is, for example, possible to use tablets containing 1 to 400 mg of the compounds 5607, 5472 and 5473, tablets containing 40 mg of 5607 CB, tablets containing 80 mg of 5472 and tablets containing 80 mg of 5473.

An example of a formula for tablets is as follows, in the case of No. 5607:

| | |
|---|---|
| 5607 (hydrochloride) | 40 mg |
| Lactose | 50 mg |
| Micro-crystalline cellulose | 40 mg |
| Talc | 5 mg |
| Magnesium stearate | 2.5 mg |

In veterinary medicine the compounds of the invention may be used for counteracting pains of various origins such as inflammatory, obstetric and surgical origin, and to relieve the apprehension of animals placed in disturbing situations.

What I claim is:

1. A 1, 3-disubstituted indole of the formula

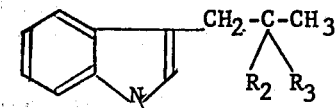

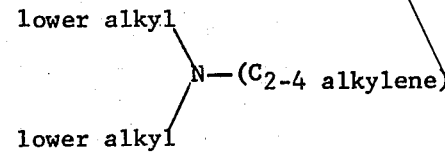

wherein $R_2$ is H and $R_3$ is OH.

2. A 1,3-distributed indole having the formula

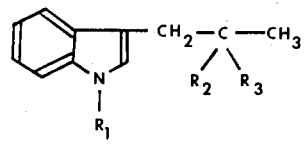

in which $R_1$ is selected from the group consisting of dimethylaminoethyl, dimethylaminopropyl, diethylaminoethyl and diethylaminopropyl and $R_2$ is hydrogen and $R_3$ is hydroxyl.

3. The compound of claim 1 in which $R_1$ is a dimethylaminoethyl group, $R_2$ is hydrogen and $R_3$ is hydroxyl and the hydrochloride thereof.

4. The compound of claim 1 in which $R_1$ is a diethylaminoethyl group, $R_2$ is hydrogen and $R_3$ is hydroxyl, and the citrate thereof.

* * * * *

UNITED STATES PATENT OFFICE
CERTIFICATE OF CORRECTION

Patent No. 3,933,853                    Dated January 20, 1976

Inventor(s) Henri Demarne

It is certified that error appears in the above-identified patent and that said Letters Patent are hereby corrected as shown below:

Claims 3 and 4, line 1: change "Claim 1" to read

--Claim 2--.

Signed and Sealed this

Tenth Day of August 1976

[SEAL]

*Attest:*

RUTH C. MASON
*Attesting Officer*

C. MARSHALL DANN
*Commissioner of Patents and Trademarks*